(12) United States Patent
Khan (10) Patent No.: US 9,192,611 B2
(45) Date of Patent: Nov. 24, 2015

(54) FORMULATIONS COMPRISING METHYLTHIONINIUM CHLORIDE

(75) Inventor: Karrar Ahmad Khan, Nottingham (GB)

(73) Assignee: WisTa Laboratories Ltd., Singapore (SG)

( * ) Notice: Subject to any disclaimer, the term of this patent is extended or adjusted under 35 U.S.C. 154(b) by 0 days.

(21) Appl. No.: 13/989,953

(22) PCT Filed: Nov. 30, 2011

(86) PCT No.: PCT/GB2011/001662
§ 371 (c)(1),
(2), (4) Date: May 28, 2013

(87) PCT Pub. No.: WO2012/072977
PCT Pub. Date: Jun. 7, 2012

(65) Prior Publication Data
US 2013/0243858 A1    Sep. 19, 2013

Related U.S. Application Data

(60) Provisional application No. 61/418,164, filed on Nov. 30, 2010.

(51) Int. Cl.
| | | |
|---|---|---|
| A61K 31/5415 | (2006.01) | |
| A61K 9/16 | (2006.01) | |
| A61K 9/20 | (2006.01) | |
| A61K 9/48 | (2006.01) | |
| C07D 279/18 | (2006.01) | |

(52) U.S. Cl.
CPC ........... *A61K 31/5415* (2013.01); *A61K 9/1652* (2013.01); *A61K 9/20* (2013.01); *A61K 9/2054* (2013.01); *A61K 9/2095* (2013.01); *A61K 9/4866* (2013.01); *C07D 279/18* (2013.01)

(58) Field of Classification Search
CPC . A61K 9/1652; A61K 9/2054; A61K 9/2095; A61K 9/20; A61K 31/5415; A61K 9/4866; C07D 279/18
USPC ................ 424/465, 474, 480, 482; 427/2.14; 514/224.8; 264/109
See application file for complete search history.

(56) References Cited

U.S. PATENT DOCUMENTS

2008/0317678 A1* 12/2008 Szymczak et al. ........... 424/10.3

FOREIGN PATENT DOCUMENTS

WO    WO 2011/036561 A2 *  3/2011

OTHER PUBLICATIONS

Remington's Pharmaceutical Sciences, 17th edn. 1985, pp. 1604-1607.*
Search Report and Written Opinion received in PCT/GB2011/01662, dated Jul. 5, 2012.
Bodman, et al., "Solubility and Properties of Two Crystalline Phases of Methylene Blue", *Journal of Chemical and Engineering Data*, vol. 12, No. 4, 1967, pp. 500-504.
Marr III, et al., "The Crystal Structure of Methylene Blue Pentahydrate" *Acta Cryst.*, B29, 1973, pp. 847-853.
Warwicker, et al., "The Crystal Structure of Methylene-blue", *Journal of the Chemical Society*, 1955, p. 2531.
Anonymous: "Phosphasal", Aug. 1, 2010 (XP002678443), retrieved from the Internet: URL: http://www.drugs.com/pro/phosphasal.html.

* cited by examiner

*Primary Examiner* — Blessing M Fubara
(74) *Attorney, Agent, or Firm* — Foley & Lardner LLP (57) ABSTRACT

Solid dosage forms of methylthioninium chloride (MTC) further comprise at least one diluent suitable for direct compression. The MTC exists in a substantially pure and stable polymorphic form. The solid dosage forms may preferably be prepared by direct compression methods.

26 Claims, 5 Drawing Sheets

FORMULATIONS COMPRISING METHYLTHIONINIUM CHLORIDE

CROSS REFERENCE TO RELATED APPLICATIONS

This application is the U.S. National Phase of PCT/GB2011/001662, filed Nov. 30, 2011, and published in English as WO 2012/072977 A2 on Jun. 7, 2012; and claims benefit of the filing date of U.S. Provisional Application No. 61/418,164, filed Nov. 30, 2010.

TECHNICAL FIELD

The present invention relates to solid dosage forms of methylthioninium chloride and to methods of preparing such solid dosage forms. In particular, in preferred embodiments the invention relates to tablet formulations in which the polymorphic form of the active ingredient is stable.

BACKGROUND ART

Methylthioninium chloride (MTC) [3,7-bisdimethylaminophenazothionium chloride, $C_{16}H_{18}ClN_3S$, 319.85 g/mol], commonly known as methylene blue, was prepared for the first time in 1876 (The Merck Index, 13th edition, Merck & Co., Inc., 2001, entry 6085). Various synthetic methods for MTC are known and have recently been summarized in WO 2006/032879. WO 2006/032879 also discloses a number of applications of methylene blue, which include use as a medical dye, as a redox indicator, as an antiseptic, for the treatment and prevention of kidney stones, and for the treatment of melanoma, malaria, and viral infections. MTC has also been used as an oxidizing agent and as an antidote in the case of carbon monoxide, nitrite and aniline poisoning.

MTC has also been proposed for treatment of mild to moderate dementia of the Alzheimer's type (DAT), also known as Alzheimer's disease (AD), a severe irreversible neurodegenerative disease resulting in complete loss of mental faculties.

For example WO96/30766 describes the use of tau aggregation inhibitors—including MTC for the treatment of various diseases of protein aggregation including AD. Other disclosures of phenothiazines in the area of neurodegenerative disorders include WO 02/075318, WO 2005/030676, WO 02/055720, WO2007110627, WO2009/060191, WO2009/044127.

MTC, in common with many solid substances useful as active pharmaceutical ingredients, exhibits polymorphism, i.e. it exists in more than one physical form, known as polymorphs, which are typically different crystalline and hydrate forms of the drug substance. Hydrates are crystalline solids containing differing amounts of water incorporated into the crystal structure.

The Fluka catalogue states in very general terms that MTC may contain up to 22% water (Fluke Catalogue 1997/1998, Fluka Chemie AG, 1997]. MTC is generally considered to exist as a trihydrate, but this was disputed as long as 80 years ago, and non-specific adsorption of water by MTC was proposed instead (H. Wales, O. A. Nelson, J. Am. Chem. Soc. 45 (1923) 1657). A pentahydrate including single crystal X-ray data was described later by several authors (J. O. Warwicker, J. Chem. Soc. (1955) 2531 and H. E. Marr III, J. M. Stewart, M. F. Chiu, Acta Cryst. B29 (1973) 847). This pentahydrate consists of π-stacked columns of MTC molecules arranged in planes perpendicular to the α-axis of the crystal. The water molecules and chloride ions are located between these layers, whereas the chloride ions are concentrated in planes almost perpendicular to the water planes and parallel to the axis of the columns. The chloride ions are coordinated with three hydrogen bonds from 3/2 water molecules. Presumably, the same structure was earlier attributed to a tetrahydrate (W. H. Taylor, Z. Krist. 91 (1935) 450).

The MTC polymorph known as "Form A" has been identified as a pentahydrate and "Form B" as a dihydrate. Form A is considered stable at high relative humidity (RH) down to approximately 35% RH. High kinetic stability of the pentahydrate (Form A) is even observed down to RH less than 20%.

Several other polymorphs of MTC, referred to as Forms C, D and E, have also been identified. It has been found that the dihydrates B and D are metastable forms over the whole range of water activity and are only kinetically favoured under certain preparation conditions. Form B seems to be the product of incomplete drying of Form A. Form D was obtained in precipitation experiments. No anhydrate form has been identified, but X-ray diffractograms include peaks that cannot be attributed to any of the five known forms. It is therefore likely that the polymorphism of MTC is even more complex than has hitherto been established.

Prior filed unpublished patent applications PCT/IB2010/002526 and PCT/IB2010/002543 relate to crystalline forms of diaminophenothiazines and provide more detailed information on the characteristic diffraction peaks of the various polymorphic forms. The disclosure of these applications (and corresponding priority documents) particularly in respect of such patterns and peaks is specifically incorporated herein.

It is known that the polymorphic forms of a drug molecule may have different chemical and/or physical properties. For example, polymorphs can differ substantially in melting point, chemical reactivity, particle size, shape, flow characteristics, caking, degree of hydration or solvation, optical and electrical properties vapour pressure, and density. As a result, certain polymorphs of a drug molecule can be more stable than others under given environmental conditions.

MTC has a number of properties which render its formulation into a dosage form quite difficult. The distinct blue colour presents processing and cleaning challenges. More significantly, the existence of numerous polymorphic forms is problematic. In particular, the physical stability of the polymorphic Form A is problematic, as during heating and/or storage it can be converted into the polymorphic Forms B and D. The interconversion of the individual crystalline polymorphic forms of MTC in a medicament, during manufacture and/or storage is undesirable as it is a general regulatory requirement that the identity of the medicament must be guaranteed throughout its entire shelf life.

The limited stability domain of all MTC polymorphic forms requires an innovative approach to formulation to produce a consistent dosage form. The product quality should be consistent and reproducible at the time of manufacture and on storage at temperatures and relative humidity levels typically encountered in most countries of the world. One may additionally seek other desirable properties in a formulation such as fast dissolution so that the tablet quickly dissolves and the medicine is available for absorption, and also properties such as good compressibility and robustness, and ease of manufacture. Accordingly, good storage stability and fast dissolution are important and desirable attributes for immediate release tablet formulations and capsules.

Processes used for tablet formulation and film coating often require the use of heat accompanied by low humidity during the drying process. Clearly, for a material such as MTC, with complex polymorphism, such processes can lead to changes in the physical form of the active ingredient, and hence potentially to instability in the performance of the product.

The most commonly used method for the preparation of solid dosage forms is wet granulation. This involves adding a granulating fluid to a powder. The granulating fluid may be water or some other solvent that is sufficiently volatile that it can subsequently be removed by drying. The granulating fluid may also include a binder. Once the solvent has been removed, the resulting mass is milled.

Wet granulation is often preferred over direct compression because wet granulation is more likely to overcome any problems associated with the physical characteristics of various ingredients in the formulation. Wet granulation provides material which has the required flow and cohesive properties necessary to obtain an acceptable solid dosage form. The content uniformity of the solid dosage form is generally improved with wet granulation because all of the granules usually contain the same amount of drug. Segregation of the drug from excipients is also avoided.

In direct compression, the individual constituents of the composition to be compressed are mixed without previous granulation and then directly compressed. Whilst this appears to be an elegant and simple process, it is difficult to obtain with it commercially usable tablets which have sufficient strength yet which also disintegrate sufficiently rapidly after administration. Also, many active substances cannot be processed by direct compression since they cannot be compressed without a granulation step.

DISCLOSURE OF THE INVENTION

The present invention provides novel formulations (tablets and capsules), particularly immediate release formulations, of MTC having one or more desirable properties such as those described above e.g. a consistent and reproducible composition at the time of manufacture, stability on storage at temperatures and relative humidity levels typically encountered in most countries of the world, fast dissolution, robustness, and ease of manufacture.

As described in more detail below, in various aspects of the invention there are provided tablet dosage forms and processes for the production thereof provided by direct compression (e.g. simple direct compression), dry granulation, or moist granulation of excipients, followed by drying and addition of the active ingredient extra-granularly. As shown in the Examples, such processes can avoid the application of heat or excessive moisture to the MTC, but nevertheless produce a formulation having one or more of the desirable properties above.

For example, it has now surprisingly been found that MTC, notably MTC of polymorphic Form A but also other Forms or mixtures of Forms, such as a mixture of Forms B and C, is particularly well suited for direct compression into solid dosage forms, in particular tablets. MTC has also been found to be stable in a directly compressed solid dosage form such as a tablet, during manufacture and storage, and is not converted into another polymorphic form (in particular Form A is not converted to the Forms B, C or D). This is in contrast to the behaviour of MTC when processed by conventional granulation processes, in which, for instance, MTC of Form A can be converted to a substantial extent into Forms B, C and/or D.

Thus, according to a first aspect of the invention there is provided a pharmaceutical composition in solid dosage form comprising, as active ingredient, MTC, said composition further comprising at least one diluent suitable for direct compression, characterised in that the MTC exists in a substantially pure and stable polymorphic form.

According to a second aspect of the invention, there is provided a process for the manufacture of a pharmaceutical composition according to the first aspect, which process comprises the direct compression of an intimate powder mixture of MTC in a substantially pure polymorphic form with at least one diluent suitable for direct compression, and optionally one or more other excipients.

According to a third aspect of the invention, there is provided a free-flowing, cohesive powder, comprising MTC in a substantially pure polymorphic form, at least one diluent suitable for direct compression, and optionally one or more other excipients, said powder being capable of being directly compressed into a pharmaceutical composition according to the first aspect.

As explained in more detail below, in various aspects and embodiments the invention also provides other pharmaceutical compositions comprising MTC in solid dosage form, the composition further comprising at least one diluent suitable for other dry compression methods e.g. based on dry granulation, or moist granulation of excipients, followed by drying and addition of the active ingredient extra-granularly. Where the term "direct compression" is used in respect of components suitable for that purpose, it will be understood that it applies mutatis mutandis to these other dry compression methods described herein.

'Dry compression', as used herein, refers to compression techniques which do not involve the use of excessive heat or moisture in respect of the active ingredient (here: MTC).

Thus the invention also provides a free-flowing, cohesive powder, comprising a compound of the invention and at least one diluent suitable for dry granulation and optionally one or more other excipients (particularly a lubricant). As explained below, this can be used in methods such as "slugging" or those using a "roller compactor". Such processes form further embodiments of the invention. On one embodiment the dry granulation is carried out by blending MTC. optionally with a lubricant, with wet-massed excipients, which are dried before the blending step.

Solid dosage forms according to the invention exhibit long term chemical and crystallographic stability of the active ingredient, MTC. The pharmaceutical compositions according to the invention have very good dissolution rates even after long term storage.

A "substantially pure" polymorphic form of MTC is one in which the predominant polymorphic form of MTC accounts for at least 80% w/w of the material, or at least 90% w/w, or at least 95% w/w. In other words, the material contains less than 20% w/w, or less than 10% w/w or less than 5% w/w of polymorphic forms other than the predominant form.

A "substantially pure and stable polymorphic form" of MTC is one in which the predominant polymorphic form remains substantially pure in the composition even after prolonged storage under controlled conditions of temperature and humidity.

Thus the MTC in the solid dosage form will substantially maintain its polymorphic identity when stored under chosen environmental conditions.

More specifically, in preferred embodiments, the predominant polymorphic form of the MTC in the composition will exhibit less than 1, 2, 3, 4, 5, 6, 7, 8, 9, or 10% conversion to polymorphic forms other than the predominant form when stored under controlled conditions for a defined period of time.

Preferred controlled conditions are storage in a blister pack (preferably one having aluminum cavity and aluminum foil)

which is thus substantially moisture-impervious. The controlled temperature is 25° C. and the controlled storage humidity is 65% RH. The defined period of time is 9 months. However preferred embodiments of the invention may demonstrate stability even at higher temperatures or different humidities (e.g. 30 or 40° C./75% RH) and longer periods e.g. 10.5 months, 12 months, 24 months, or 36 months.

The conversion between polymorphic forms may conveniently be assessed by X-ray powder diffractograms. For this purpose the blister pack is opened and the tablet cores are slightly crushed in order to obtain a suitable powder that can be prepared on an XRPD sample holder. The different polymorphs show characteristic signals in the 2q range below 12°, which will be essentially free of signals from the excipients. An evaluation of the XRPD signals in this 2q range permits an unambiguous assignment of the solid state polymorphic forms of MTC in the sample. As an initial assessment, when testing a dosage form of substantially pure Form A pentahydrate, the absence of any signals from lower hydrates may be verified (here the absence of a signal would typically be defined by a signal intensity which does not exceed three times the noise).

The examples below show analysis of polymorphs using a Bruker D8 Advance with LynxEye detector with measurements performed in the Bragg-Brentano reflection geometry with Cu Kα radiation ($\lambda \approx 1.54180$ Å) at 40 kV/40 mA. Data points were collected with 0.02 step size in 2θ and 37s accumulation time per step. The samples were prepared on silicon single crystal sample holders with 1.0 mm depth and 12 mm diameter. All samples were rotated at 30 rpm during the measurement.

Initial assessment may be followed by quantification of each polymorph (if present) by use of appropriate reference measurements of mixtures of different polymorphs.

Thus a further aspect of the invention provides for use of a system comprising a diluent and direct compression (or dry granulation) for enhancing the stability of a substantially pure MTC polymorph in a pharmaceutical composition.

In preferred embodiments of the invention, the MTC is used in polymorph Form A. As noted above, use of the present invention minimises conversion of Form A to the Forms B, C or D.

The amount of MTC in the uncoated composition is generally more than about 10% w/w, but can be more than 20%, or more than 30% w/w. The amount of MTC is generally less than about 70% w/w, and usually less than 60% or less than 50% w/w. Typically, the amount of MTC in the uncoated composition is thus from about 10% w/w (or 20% or 30%) to about 70% w/w (or 60% or 50%). Where a coating is applied to the composition, as described below, the overall weight of the composition is increased and thus the percentage MTC in the overall composition is somewhat reduced.

MTC is not inherently compressible and thus requires addition of suitable diluents to aid compression.

The pharmaceutical compositions of the invention therefore commonly comprise at least 15% w/w, more commonly at least 20%, at least 30%, at least 40% or at least 50% w/w of diluent(s).

Diluents that may be used include one or more of microcrystalline cellulose, lactose, mannitol, calcium salts such as calcium phosphate dibasic, calcium sulphate and calcium carbonate, and sugars such as lactose, sucrose, dextrose and maltodextrin.

Preferred diluents are microcrystalline cellulose, lactose and mannitol. Spray-dried forms of lactose and mannitol are particularly suitable forms of those compounds.

It has unexpectedly been found that when MTC of a particular polymorphic form (e.g. Form A) is formulated with direct compression diluents such as one or more of microcrystalline cellulose, spray dried lactose, anhydrous lactose and mannitol, the resulting solid dosage forms are stable in the sense that the polymorphic form of the MTC is preserved, and the MTC remains chemically stable, even after extended storage. The invention thus provides a method of preparing low-, medium- or high-dose MTC tablets that are stable and have acceptable dissolution profiles, acceptable degrees of hardness and resistance to chipping, as well as a short disintegration time.

The pharmaceutical composition will generally also include a lubricant. Examples of lubricants include magnesium stearate, calcium stearate, sodium stearyl fumarate, stearic acid, glycerylbehaptate, polyethylene glycol, ethylene oxide polymers (for example, those available under the registered trademark Carbowax from Union Carbide, Inc., Danbury, Conn.), sodium lauryl sulphate, magnesium lauryl stearate, mixtures of magnesium stearate with sodium lauryl sulphate, and hydrogenated vegetable oil. Preferred lubricants include calcium stearate, magnesium stearate and sodium stearyl fumarate. Most preferred as the lubricant is magnesium stearate. Lubricants generally comprise from about 0.5 to about 5.0% of the total (uncoated) tablet weight. The amount of lubricant employed is generally from about 1.0 to about 2.0%, preferably 0.5 to 2.0% w/w.

In addition to the diluent(s) and lubricant(s), other conventional excipients may also be present in the pharmaceutical compositions of the invention. Such additional excipients include disintegrants, binders, flavouring agents, colours and glidants. Some excipients can serve multiple functions, for example as both binder and tablet disintegrant.

A tablet disintegrant may be present in an amount necessary to achieve rapid dissolution.

Disintegrants are excipients which oppose the physical forces of particle bonding in a tablet or capsule when the dosage form is placed in an aqueous environment. Examples of disintegrants include crosslinked polyvinylpyrrolidone, sodium starch glycolate, crosslinked sodium carboxymethyl cellulose (sodium croscarmellose), and pregelatinized starch. Generally the amount of disintegrant can be from 0 to about 25% w/w, more commonly from about 1% to about 15% w/w, and usually less than 10% or less than 5% w/w, of the composition.

Binders are excipients which contribute to particle adhesion in a solid formulation. Examples of binders include cellulose derivatives (carboxymethylcellulose, hydroxypropyl methylcellulose, hydroxypropyl cellulose, hydroxyethylcellulose, ethylcellulose, microcrystalline cellulose) and sugars such as lactose, sucrose, dextrose, glucose, maltodextrin, and mannitol, xylitol, polymethacrylates, polyvinylpyrrolidone, sorbitol, pregelatinized starch, alginic acids, and salts thereof such as sodium alginate, magnesium aluminum silicate, polyethylene glycol, and the like. Generally, the amount of binder can vary widely, e.g. from 0% to 95% w/w of the composition. As noted above, excipients may serve multiple functions. For instance, the tabletting diluent may also serve as a binder.

Glidants are substances added to a powder to improve its flowability. Examples of glidants include magnesium stearate, colloidal silicon dioxide (such as the grades sold as Aerosil), starch and talc. Glidants may be present in the pharmaceutical composition at a level of from 0 to about 5% w/w. Again, however, it should be noted that excipients may serve multiple functions. The lubricant, for example magnesium stearate, may also function as a glidant.

Examples of colours that may be incorporated into the pharmaceutical compositions of the invention include titanium dioxide and/or dyes suitable for food such as those known as FD&C dyes and natural colouring agents. A colouring agent is unlikely to be used in the powder mixture that is compressed in accordance with the second aspect of the invention, but may form part of a coating applied to the composition, as described below, in which case the colouring agent may be present in the film coat in an amount up to about 2.0% w/w.

Where the composition is a tablet, this is desirably coated with a conventional film coating which imparts toughness, ease of swallowing, and an elegant appearance to the final product. Many polymeric film-coating materials are known in the art. A preferred film-coating material is hydroxypropyl-methylcellulose (HPMC) or polyvinyl alcohol-part hydrolysed (PVA). HPMC and PVA may be obtained commercially, for example from Colorcon, in coating formulations containing excipients which serve as coating aids, under the registered trademark Opadry. Opadry formulations may contain talc, polydextrose, triacetin, polyethyleneglycol, polysorbate 80, titanium dioxide, and one or more dyes or lakes. Other suitable film-forming polymers may also be used, including hydroxypropylcellulose, vinyl copolymers such as polyvinyl pyrollidone and polyvinyl acetate, and acrylate-methacrylate copolymers. Use of a film coating is beneficial for ease of handling and because a blue coloured uncoated core may stain the inside of the mouth during swallowing. Coating also improves light stability of the dosage form.

Coating of the tablets may conveniently be carried out using a conventional coating pan. In preferred embodiments of the process, the coating pan is pre-heated using heated inlet air until the exhaust temperature reaches 35-55° C., more preferably 40-50° C. This may typically require application of heated inlet air at an inlet temperature of 45-75° C., preferably 50-65° C., for 10-15 minutes. The MTC tablets are then added to the coating pan and the aqueous film coat applied. The spray rate is controlled such that the bed temperature is maintained at 38-48° C., more preferably 42-44° C., until the desired weight gain (coating weight) has been achieved.

One aspect of the present invention pertains to a method of treatment or prophylaxis of a disease condition in a patient, comprising administering to said patient a therapeutically-effective amount of a solid dosage form composition as described herein.

One embodiment of the present invention pertains to a method of treatment or prophylaxis of a tauopathy condition in a patient, comprising administering to said patient a therapeutically-effective amount of a solid dosage form composition as described herein.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim preserving health by helping to delay, mitigate or avoid that particular condition.

Those skilled in the art are familiar with the spectrum of diseases known as "tauopathies". As well as Alzheimer's disease (AD), the pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include frontotemporal dementia (FTD); FTD with parkinsonism linked to chromosome 17 (FTDP-17); behavioural variant FTD (bvFTD); progressive nonfluent aphasia (PNFA) Josephs, K A, Petersen, RC, Knopman, D S, et al. (2006) Clinicopathologic analysis of frontotemporal and corticobasal degenerations and PSP. Neurology 66:41-48; disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD); Dementia with Argyrophilic grains (AgD); Dementia pugilistica (DP) wherein despite different topography, NFTs are similar to those observed in AD (H of P. R., Bouras C., Buee L., Delacourte A., Pen D. P. and Morrison J. H. (1992) Differential distribution of neurofibrillary tangles in the cerebral cortex of dementia pugilistica and Alzheimer's disease cases. Acta Neuropathol. 85, 23-30). Others are discussed in an article by Wischik et al. (in 'Neurobiology of Alzheimer's Disease', 2nd Edition, 2000, Eds. Dawbarn, D. and Allen, S. J., The Molecular and Cellular Neurobiology Series, Bios Scientific Publishers, Oxford; especially Table 5.1).

Abnormal tau in NFTs is found also in Down's Syndrome (DS) (Flament S., Delacourte A. and Mann D. M. A. (1990) Phosphorylation of tau proteins: a major event during the process of neurofibrillary degeneration. A comparative study between AD and Down's syndrome. Brain Res., 516, 15-19). Also Dementia with Lewy bodies (DLB) (Harrington, C. R., Perry, R. H., Perry, E. K., Hurt, J., McKeith, I. G., Roth, M. & Wischik, C. M. (1994) Senile dementia of Lewy body type and Alzheimer type are biochemically distinct in terms of paired helical filaments and hyperphosphorylated tau protein. Dementia 5, 215-228). Tau-positive NFTs are also found in Postencephalitic parkinsonism (PEP) (H of P. R., Charpiot, A., Delacourte A., Buee, L., Purohit, D., Perl D. P. and Bouras, C. (1992) Distribution of neurofibrillary tangles and senile plaques in the cerebral cortex in postencephalitic parkinsonism. Neurosci. Lett. 139, 10-14). Glial tau tangles are observed in Subacute sclerosing panencephalitis (SSPE) (Ikeda K., Akiyama H., Kondo H., Arai T., Arai N. and Yagishita S. (1995) Numerous glial fibrillary tangles in oligodendroglia in cases of subacute sclerosing panencephalitis with neurofibrillary tangles. Neurosci. Lett., 194, 133-135).

Other tauopathies include Niemann-Pick disease type C (NPC) (Love, S., Bridges, L. R. & Case, C. P. (1995), Brain, 118, 119-129); Sanfilippo syndrome type B (or mucopolysaccharidosis III B, MPS III B) (Ohmi, K., Kudo, Ryazantsev, S., et al. (2009) *PNAS*, 106, 8332-8337; myotonic dystrophies (DM), DM1 (Sergeant, N., Sablonniere, B., Schraen-Maschke, S., et al. (2001) *Human Molecular Genetics*, 10, 2143-2155 and references cited therein) and DM2 (Maurage, C. A., Udd, B., Ruchoux, M. M., et al. (2005) *Neurology*, 65, 1636-1638) and Lafora disease (Greene, V., and Papasozomenos, S. C. (1987) *J. Neuropathol. Exp. Neurol.* 46:345, and Pun, R, Suzuki, T, Yamakawa, K, Ganesh, S (2009) Hyperphosphorylation and aggregation of tau in laforin deficient mice, an animal model for Lafora disease. *J. Biol. Chem.* 284:22657-22663).

Additionally there is a growing concensus in the literature that a tau pathology may also contribute more generally to cognitive deficits and decline, including in mild cognitive impairment (MCI) (see e.g. Braak, H., Del Tredici, K, Braak, E. (2003) Spectrum of pathology. In Mild cognitive impairment: Aging to Alzheimer's disease edited by Petersen, R. C.; pp. 149-189).

All of these diseases, which are characterized primarily or partially by abnormal tau aggregation, are referred to herein as "tauopathies" or "diseases of tau protein aggregation".

In this and all other aspects of the invention relating to tauopathies, preferably the tauopathy is selected from the list consisting of the indications above, i.e., AD, Pick's disease, PSP, FTD, FTDP-17, DDPAC, PPND, Guam-ALS syndrome, PNLD, and CBD and AgD, DS, SSPE, DP, PEP, DLB and MCI.

In one preferred embodiment the tauopathy is Alzheimer's disease (AD).

In other embodiments the compositions of the invention may be used in the treatment or prophylaxis of TDP-43 proteinopathies e.g. frontotemporal lobe dementia associated with TDP-43 (FTLD-TDP43), amyotrophic lateral sclerosis (ALS) and overlapping syndromes, and semantic dementia and FTDP-17 (Chen-Plotkin, A S, Lee, V M Y, Trojanowski, J Q (2010) TAR DNA-binding protein 43 in neurodegenerative disease. Nature Reviews Neurology 6:211-220).

One aspect of the present invention pertains to a solid dosage form composition, as described herein, for use in a method of treatment or prophylaxis (e.g. of a tauopathy condition or TDP-43 proteinopathy) of the human or animal body by therapy.

One aspect of the present invention pertains to use of a solid dosage form composition, as described herein, in the manufacture of a medicament for use in the treatment or prophylaxis of the condition.

A further embodiment is a method of treatment or prophylaxis of a disease of protein aggregation as described herein, which method comprises administering to a subject a solid dosage form composition such as to inhibit the aggregation of the protein (e.g. tau protein) associated with said disease state.

In a further embodiment there is disclosed a solid dosage form composition of the invention for use in a method of treatment or prophylaxis of a disease of protein aggregation as described above, which method comprises administering to a subject the solid dosage form composition such as to inhibit the aggregation of the protein associated with said disease state.

In a further embodiment there is disclosed use of a solid dosage form composition of the invention in the preparation of a medicament for use in a method of treatment or prophylaxis of a disease of protein aggregation as described above, which method comprises administering to a subject the composition such as to inhibit the aggregation of the protein associated with said disease state.

In one embodiment there is disclosed a method of regulating the aggregation of a protein in the brain of a mammal, which aggregation is associated with a disease state as described above, the treatment comprising the step of administering to said mammal in need of said treatment, a prophylactically or therapeutically effective amount of an inhibitor of said aggregation, wherein the inhibitor is a solid dosage form composition of the invention.

One aspect of the invention is a method of inhibiting production of protein aggregates (e.g. in the form of paired helical filaments (PHFs), optionally in neurofibrillary tangles (NFTs)) in the brain of a mammal, the treatment being as described herein.

In one aspect the invention provides a drug product for the treatment of a disease state associated with protein aggregation in a mammal suffering therefrom, comprising a container labeled or accompanied by a label indicating that the drug product is for the treatment of said disease, the container containing one or more dosage units each comprising a solid dosage form composition of the invention.

A first embodiment of the manufacturing process of the second aspect of this invention is simple direct compression. In this embodiment, the tablet ingredients, i.e. MTC, diluent(s) and other optional excipients, are blended together in solid, particulate form to create an intimate mixture, e.g. in a tumbling blender, and then compressed using a tablet machine.

In a second embodiment of the method, the composition is prepared by a dry granulation process. Dry granulation refers to the process of granulating without the use of granulating fluids. In order for a material to be dry-granulated, at least one of its constituents, either the active ingredient or a diluent, must have cohesive properties. Dry granulation may be performed by a process known as "slugging". In "slugging", the material to be granulated is first made into a large compressed mass or "slug", typically using a tablet press with large flat-faced tooling (an example of a linear press is illustrated in U.S. Pat. No. 4,880,373). A fairly dense slug may be formed by allowing sufficient time for the air to escape from the material to be compacted. Compressed slugs are then milled through a desired mesh screen manually or automatically as, for example, by way of a comminuting mill. Formation of granules by "slugging" is also known as precompression. When tablets are made from the granulated slugged material, the process is referred to as the "double compression method".

Dry granulation may also be performed using a "roller compactor". In a roller compactor, material particles are consolidated and densified by passing the material between two high-pressure rollers. The densified material from a roller compactor is then reduced to a uniform granule size by milling. The uniform granules may then be mixed with other substances, such as a lubricant, to tablet the material (as, for example, by way of a rotary tableting machine). In addition to pharmaceutical use, roller compaction is used in other industries, such as the food industry, animal feed industry and fertilizer industry.

Dry granulation is nowadays generally understood to mean roller compaction or slugging, and is well known to those skilled in the art (see, for instance, Pharmaceutical Dosage Forms: Tablets (Lieberman, Lachman, and Schwartz (Eds); Marcel Dekker, Inc, 2nd Edition, 1989) and Remington's Pharmaceutical Sciences (A. R. Gennaro (Ed); Mack Publishing Co, Easton, Pa., 18th edition, 1990)).

In a further embodiment of the invention, MTC tablets are prepared by moist granulation of the excipients and incorporation of the MTC extra-granularly. Typically such a process involves wet massing diluents such as lactose and/or microcrystalline cellulose with water, optionally with the addition of a binder such as polyvinyl pyrrolidone. The wet mass is passed through a mesh and dried to form granules. The MTC and any remaining excipients, such as a lubricant, are then blended with the dry granules and compressed to form tablets.

In further aspects of the invention, there are provided capsules comprising MTC which has been formulated with diluents and other optionally other excipients as described herein. Such capsules may be prepared from materials well known in the art e.g. Gelatin, Gelatin\PEG, HPMC and so on—see "Pharmaceutical Capsules; $2^{nd}$ Revised Edition" Podczeck & Jones (Eds), Pharmaceutical Press 2004.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLE 1

The physicochemical properties of different solid state forms of MTC 1.1 X-Ray Powder Diffraction (XRPD) Studies of MTC Hydrates (solid state forms)

X-ray powder diffractograms were obtained using a Bruker D8 Advance diffractometer with LynxEye detector. Measurements were performed in the Bragg-Brentano reflection geometry with Cu Kα radiation (λ=1.54180 Å) at 40 kV/40 mA. Data points were collected with 0.02 step size in 2θ and 37s accumulation time per step. The samples were prepared on silicon single crystal sample holders with 1.0 mm depth and 12 mm diameter. All samples were rotated at 30 rpm during the measurement.

FIGS. 1A-1E show respectively the X-ray diffractograms of Forms A-E of MTC.

For each of Forms A-E, Tables 1A-1E list the peaks that occur in the diffractograms (vs=very strong intensity; s=strong intensity; m=medium intensity; w=weak intensity).

TABLE 1A

| | Form A | |
|---|---|---|
| Angle 2Θ [°] | d value [Å] | Rel. Intensity (qualitative) |
| 5.7 | 15.5 | s |
| 9.3 | 9.6 | vs |
| 9.7 | 9.2 | s |
| 10.8 | 8.2 | s |
| 11.4 | 7.8 | w |
| 14.6 | 6.0 | w |
| 18.7 | 4.74 | s |
| 19.4 | 4.58 | m |
| 20.4 | 4.35 | w |
| 21.8 | 4.08 | w |
| 22.0 | 4.04 | w |
| 24.6 | 3.61 | w |
| 25.6 | 3.48 | s |
| 26.2 | 3.40 | m |
| 27.4 | 3.26 | w |
| 28.1 | 3.18 | s |
| 28.5 | 3.13 | m |
| 29.2 | 3.05 | w |
| 30.6 | 2.92 | w |
| 33.3 | 2.69 | w |
| 34.2 | 2.63 | w |
| 35.8 | 2.51 | w |
| 38.4 | 2.35 | w |
| 40.5 | 2.23 | w |
| 41.3 | 2.18 | w |
| 44.9 | 2.02 | w |
| 47.4 | 1.92 | w |

Characteristic 2Θ values (±0.1°) for Form A are thus some or all of 5.7°, 9.3°, 9.7°, 10.8°, 18.7°, 25.6° and 28.1°.

TABLE 1B

| | Form B | |
|---|---|---|
| Angle 2Θ [°] | d value [Å] | Rel. Intensity (qualitative) |
| 5.8 | 15.1 | s |
| 6.7 | 13.1 | m |
| 11.2 | 7.9 | s |
| 16.0 | 5.52 | m |
| 16.9 | 5.25 | w |
| 25.2 | 3.53 | s |
| 26.5 | 3.36 | s |
| 28.3 | 3.16 | m |

Characteristic 2Θ values (±0.1°) for Form B are thus some or all of 5.8°, 11.2°, 25.2° and 26.5°.

TABLE 1C

| | Form C | |
|---|---|---|
| Angle 2Θ [°] | d value [Å] | Rel. Intensity (qualitative) |
| 8.1 | 10.9 | vs |
| 11.2 | 7.9 | s |
| 11.7 | 7.6 | w |
| 16.2 | 5.47 | s |
| 17.6 | 5.05 | m |
| 17.8 | 4.98 | s |
| 18.4 | 4.81 | m |
| 20.5 | 4.33 | w |
| 22.5 | 3.96 | w |
| 24.1 | 3.70 | m |
| 24.4 | 3.65 | s |
| 25.9 | 3.44 | s |
| 27.2 | 3.28 | s |
| 28.8 | 3.10 | w |
| 29.5 | 3.03 | w |
| 30.0 | 2.98 | m |
| 30.8 | 2.90 | m |
| 31.4 | 2.85 | m |
| 33.0 | 2.72 | s |
| 34.2 | 2.62 | w |
| 36.0 | 2.49 | w |
| 36.7 | 2.45 | w |
| 37.4 | 2.41 | w |
| 39.7 | 2.27 | m |
| 42.5 | 2.13 | w |
| 42.9 | 2.11 | w |
| 45.3 | 2.00 | m |
| 47.9 | 1.90 | w |
| 49.4 | 1.85 | w |

Characteristic 2Θ values (±0.1°) for Form C are thus some or all of 11.2°, 16.2°, 17.8°, 24.4°, 25.9°, 27.2° and 33.0°.

TABLE 1D

| | Form D | |
|---|---|---|
| Angle 2Θ [°] | d value [Å] | Rel. Intensity (qualitative) |
| 6.0 | 14.7 | m |
| 7.0 | 12.6 | m |
| 8.6 | 10.3 | m |
| 9.8 | 9.1 | w |
| 10.4 | 8.5 | m |
| 12.0 | 7.4 | s |
| 14.4 | 6.1 | m |
| 16.3 | 5.44 | w |
| 17.2 | 5.16 | w |
| 18.1 | 4.90 | w |
| 19.6 | 4.53 | w |
| 20.8 | 4.27 | m |
| 21.2 | 4.18 | w |
| 21.8 | 4.08 | m |

TABLE 1D-continued

Form D

| Angle 2Θ [°] | d value [Å] | Rel. Intensity (qualitative) |
|---|---|---|
| 22.3 | 3.98 | m |
| 23.7 | 3.76 | m |
| 24.4 | 3.64 | m |
| 25.3 | 3.53 | s |
| 25.7 | 3.47 | s |
| 27.5 | 3.25 | s |
| 28.5 | 3.14 | m |
| 29.1 | 3.07 | m |
| 30.4 | 2.94 | m |
| 31.8 | 2.81 | m |
| 35.0 | 2.57 | w |
| 39.2 | 2.30 | w |
| 41.4 | 2.18 | w |
| 46.5 | 1.95 | w |

Characteristic 2Θ values (±0.1°) for Form D are thus some or all of 12.0°, 25.3°, 25.7° and 27.5°.

TABLE 1E

Form E

| Angle 2Θ [°] | d value [Å] | Rel. Intensity (qualitative) |
|---|---|---|
| 9.0 | 9.8 | s |
| 12.5 | 7.1 | m |
| 14.1 | 6.3 | s |
| 14.4 | 6.1 | w |
| 18.1 | 4.91 | m |
| 20.8 | 4.27 | w |
| 21.8 | 4.08 | w |
| 22.2 | 4.01 | w |
| 23.3 | 3.82 | s |
| 24.6 | 3.62 | s |
| 25.2 | 3.54 | s |
| 26.0 | 3.43 | s |
| 27.3 | 3.27 | w |
| 28.4 | 3.14 | w |
| 29.6 | 3.02 | w |
| 30.0 | 2.98 | w |
| 30.7 | 2.92 | w |
| 31.5 | 2.84 | w |
| 32.0 | 2.79 | w |
| 33.2 | 2.70 | w |
| 38.2 | 2.35 | w |
| 39.6 | 2.27 | w |
| 41.8 | 2.16 | w |
| 45.2 | 2.00 | w |
| 47.1 | 1.93 | w |

Characteristic 2Θ values (±0.1°) for Form E are thus some or all of 9.0°, 14.1°, 23.3°, 25.2° and 26.0°.

1.2 Thermogravimetry (TG)

TG and TG-FTIR of hydrate form A consistently indicated a weight loss of 21.7%, which corresponds with good approximation to 5 molecules of water per molecule of MTC. The separation between water loss and decomposition was much more distinct in TG than in TG-FTIR, which can be explained by the different measurement setup (open pan versus pan with micro hole).

1.3 Differential Scanning Calorimetry (DSC) of the MTC Pentahydrate

Figure 1A:
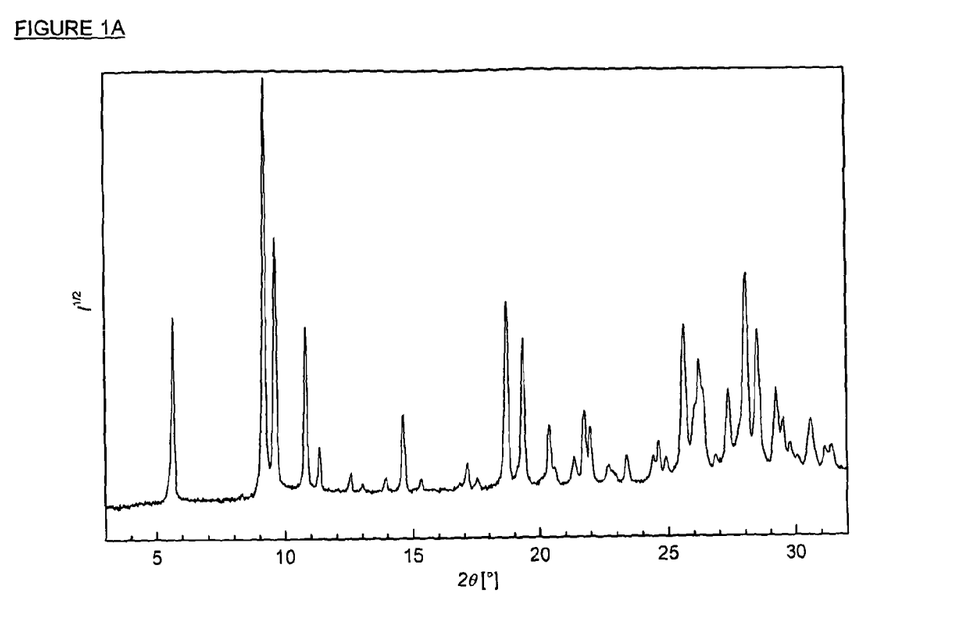
FIGS. 1A-1E show respectively the X-ray diffractograms of Forms A-E of MTC.
Figure 1B:
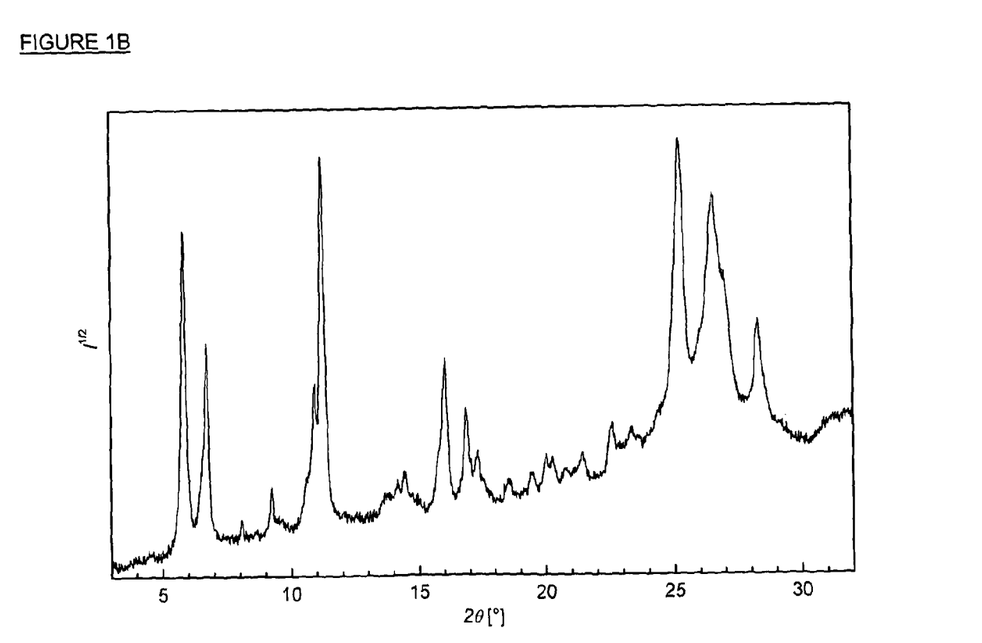
Figure 1C:
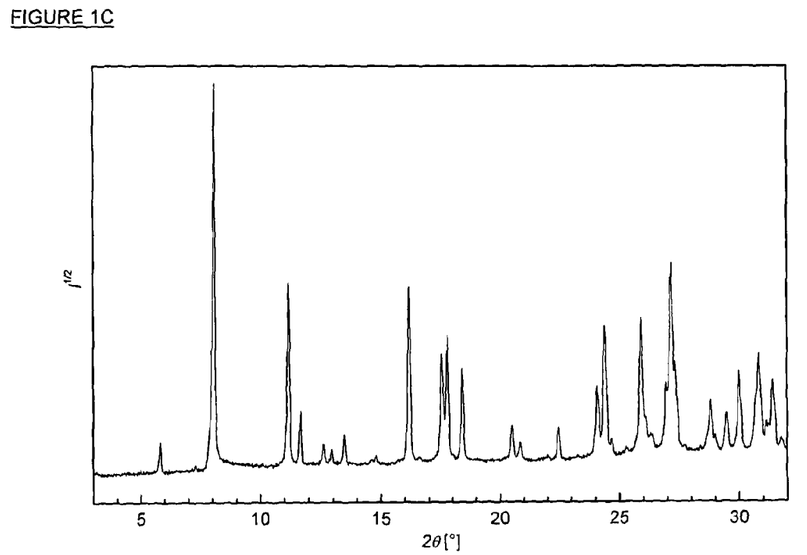
Figure 1D:
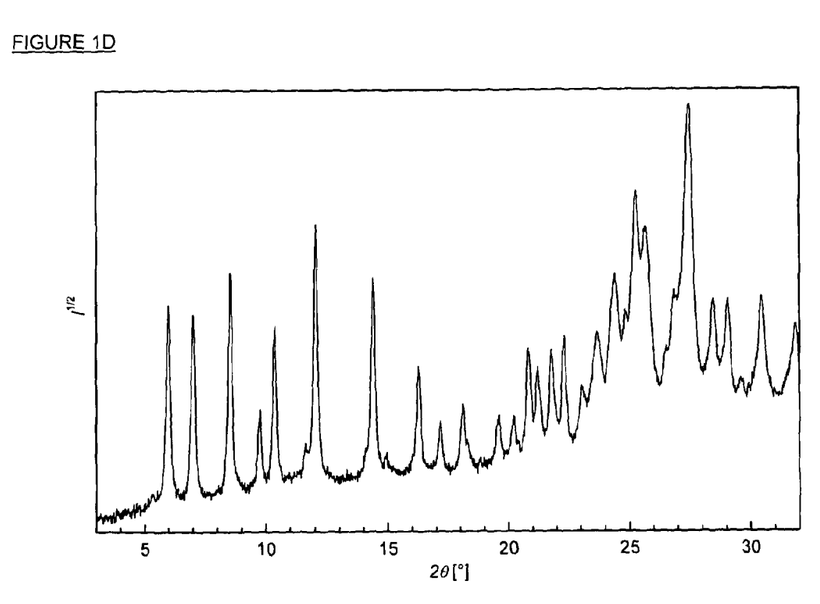
Figure 1E:
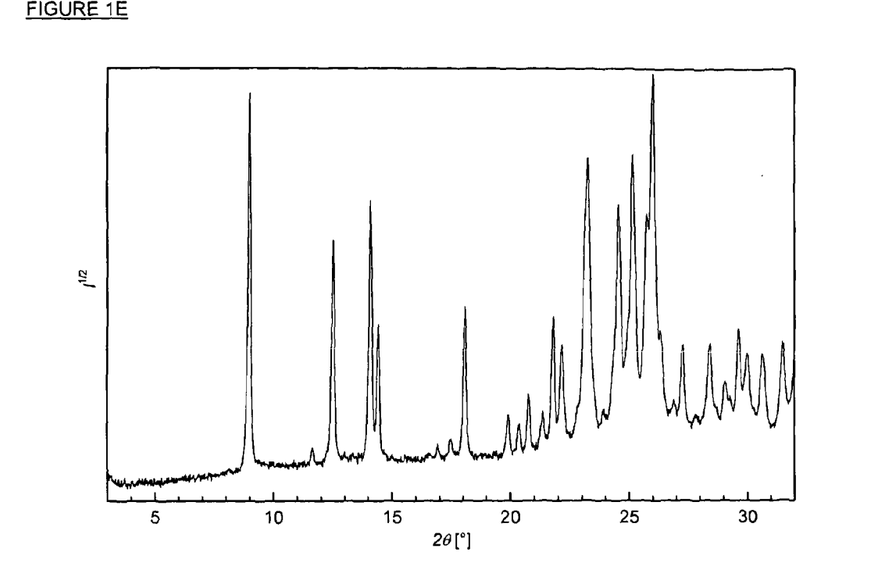
Figure 2:
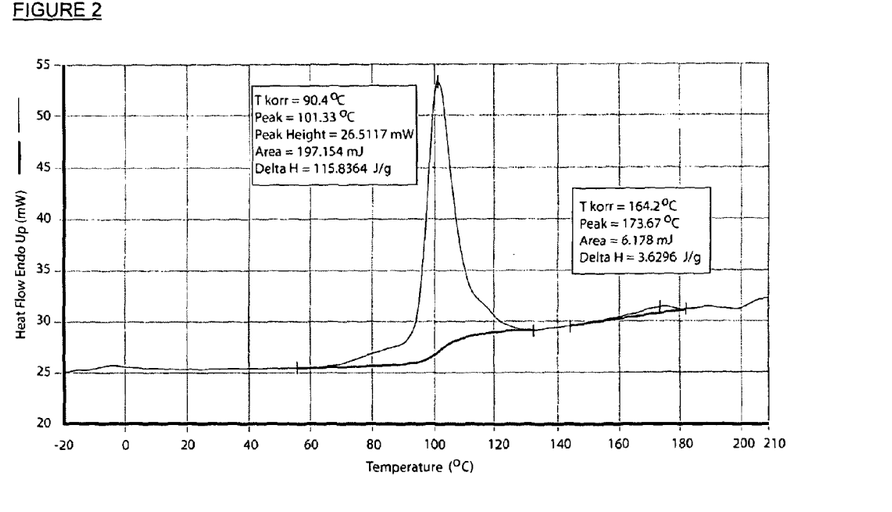
FIG. 2 shows the result of DSC measurement on a sample of MTC pentahydrate.

A DSC measurement was performed with a sample of MTC pentahydrate in a closed gold pan with a scanning rate of 100 K/min (see FIG. 2). An exothermic event was observed between approximately 75° C. and 125° C. with a corrected peak temperature at 90° C. This signal is attributable to the loss of water of hydration (ΔH=116 J/g). A much smaller, broadened peak was observed between approximately 150° C. and 180° C. which can be attributed to the dissolution of the remaining solid in the liquid phase. Above 190° C. there is evidence of decomposition (exothermic signals).

EXAMPLE 2

Thermodynamic Stability of MTC Hydrates

The thermodynamic stability of MTC hydrates is defined for a given set of environmental conditions such as temperature (T) and relative humidity (RH).

Figure 3:
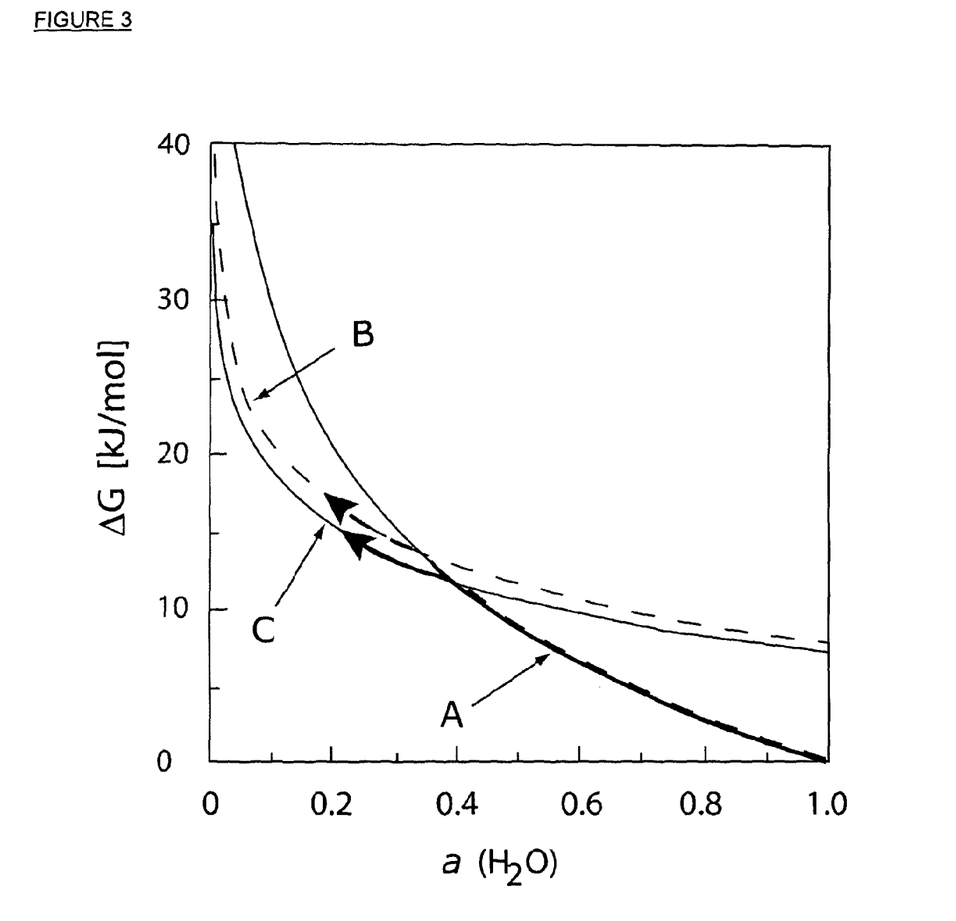
FIG. 3 shows the free energy of Forms A, B and C as a function of RH at a fixed T (25° C.)

FIG. 3 shows the free energy of Forms A, B and C as a function of RH at a fixed T (25° C.). The hydrate with the lowest ΔG represents the thermodynamically stable form. It can be seen that Form A is most stable down to a RH of ca. 40% (a($H_2O$)=0.4). Below this value, Form C is most stable. The dashed line of Form B always lies above the curve of Form C. Thus, Form B is less stable than Form C. However, the curve of Form B crosses the curve of Form A at a($H_2O$) =0.35, ie below this value Form B is more stable than Form A.

It can be seen that MTC Form B is not thermodynamically stable, though it is kinetically stable in a certain range of T and RH. Form A is thermodynamically stable at high RH, and at relatively low T. Form A may also exist as a metastable state in a broader range of T and RH.

Other hydrate Forms (ie C, D, and E) become thermodynamically most stable outside this range. However, when the borders of the stability domain of Form A are crossed, the transformation into the Form which is most stable (which is Form C) may be kinetically hindered (red arrow in FIG. 3). Form A may then transform into another form, which is kinetically more easily accessible and thermodynamically more stable than A under the given conditions of T and RH (green arrow in FIG. 3). This is the case for Form B, which is nevertheless less stable than Form C at any T and RH.

From a thermodynamic point of view, Form B can transform into Form C (and probably even Form D). There is a risk that on prolonged storage and during processing such as film coating, transformation of Form B into Form C or D could also occur.

Figure 4:
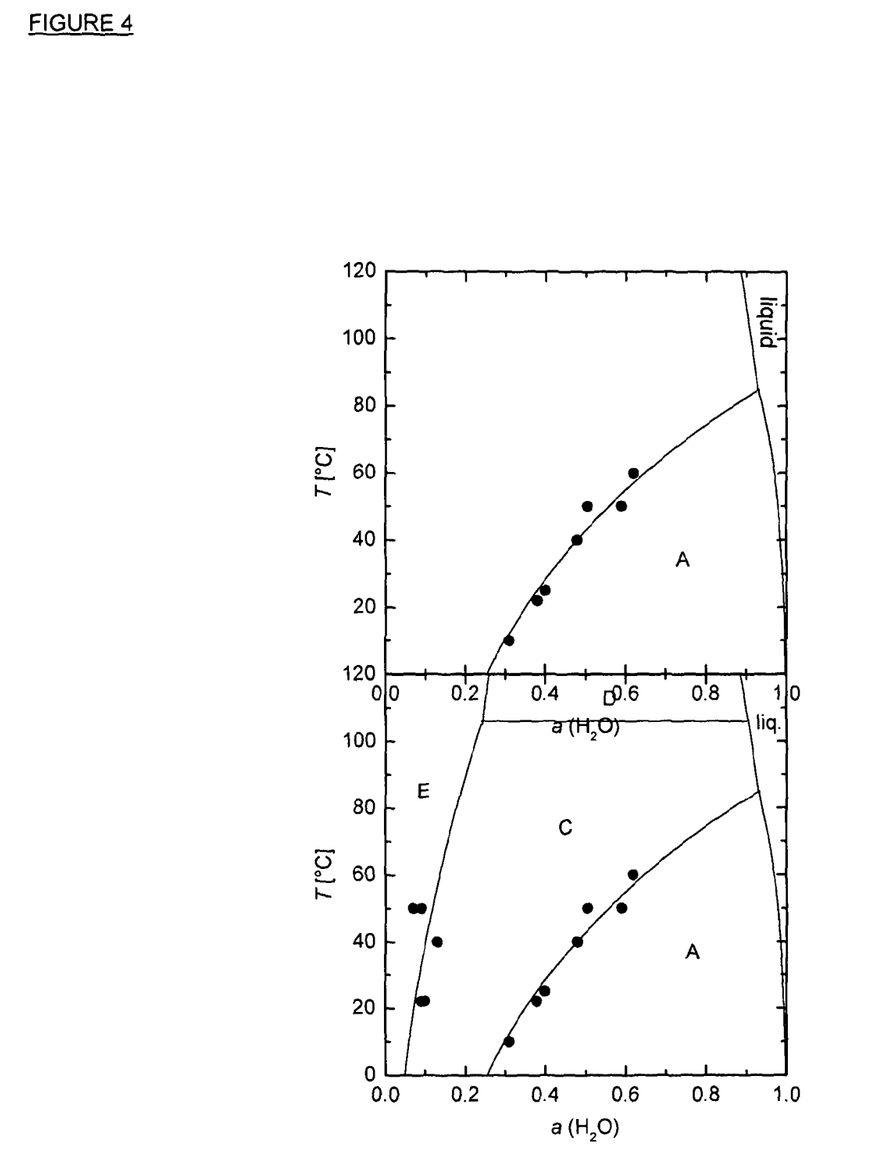
FIG. 4 shows the stability domain of MTC Form A.

FIG. 4 shows the stability domain of MTC Form A. The shaded area represents all combinations of water activity (RH) and temperature at which Form A is thermodynamically stable. The black dots represent experimental data points for the equilibrium T and RH values for the transformation between form A and form C. The Figure shows that Form A is relatively unstable below 50% RH at 40° C. and also below 40% RH at 25° C.

EXAMPLE 3

Preparation of MTC Tablets by Direct Compression

Tablets having the following compositions were prepared by a direct compression method:

| | Tablet strength (mg MTC/tablet) | | | |
|---|---|---|---|---|
| | 50 mg | 75 mg | 100 mg | 125 mg |
| Ingredient | mg/tablet | | | |
| MTC (free base equivalent) | 73.61 | 110.41 | 147.22 | 184.02 |
| Microcrystalline cellulose (Avicel PH 102) | 230.00 | 230.00 | 230.00 | 287.50 |
| Spray-dried lactose | 127.39 | 90.59 | 53.78 | 67.23 |
| Crosslinked polyvinylpyrrolidone | 15.00 | 15.00 | 15.00 | 18.75 |
| Magnesium stearate | 4.00 | 4.00 | 4.00 | 5.00 |
| TOTAL TABLET WEIGHT/mg | 450 | 450 | 450 | 562.5 |

The MTC (Form A), microcrystalline cellulose, spray-dried lactose, cross-linked polyvinylpyrrolidone and magnesium stearate were blended in a tumbling blender, and then compressed using a tablet machine.

Similar formulations may be prepared by a dry granulation method. The mix of microcrystalline cellulose, spray-dried lactose, cross-linked polyvinylpyrrolidone and magnesium stearate can be dry granulated using a roller compactor and then milled, e.g. with an oscillating granulator. In that case, half of the magnesium stearate is used prior to roller compaction and half of the magnesium stearate may be added to the granulation and blended prior to compression on a conventional tablet machine. The tablet cores may then be film coated with an aqueous suspension of Opadry blue (registered trademark of Colorcon for a series of film coating systems).

EXAMPLE 4

Preparation of MTC Tablets by Direct Compression

Tablets having the following compositions were prepared by a direct compression method:

|  | Tablet strength (mg MTC/tablet) | | | |
|---|---|---|---|---|
|  | 50 mg | 75 mg | 100 mg | 125 mg |
| Ingredient | mg/tablet | | | |
| MTC (free base equivalent) | 73.61 | 110.41 | 147.22 | 184.02 |
| Spray-dried mannitol | 357.39 | 320.59 | 283.78 | 354.73 |
| Crosslinked polyvinylpyrrolidone | 15.00 | 15.00 | 15.00 | 18.75 |
| Magnesium stearate | 4.00 | 4.00 | 4.00 | 5.00 |
| TOTAL TABLET WEIGHT/mg | 450 | 450 | 450 | 562.5 |

The MTC (Form A), microcrystalline cellulose, spray-dried mannitol, crosslinked polyvinylpyrrolidone and magnesium stearate were blended in a tumbling blender then compressed using a tablet machine.

Similar formulations may be prepared by a dry granulation method. The mix of microcrystalline cellulose, spray-dried lactose, cross-linked polyvinylpyrrolidone and magnesium stearate can also be dry granulated using a roller compactor and then milled with an oscillating granulator using a 20 mesh screen. In that case, half of magnesium stearate is used prior to roller compaction and half of the magnesium stearate may be added to the granules and blended prior to compression on a conventional tablet machine. The tablet cores may then be film coated with an aqueous suspension of Opadry blue (registered trademark of Colorcon for a series of film coating systems).

EXAMPLE 5

Preparation of MTC Tablets by Direct Compression

Tablets having the following compositions were prepared by a direct compression method:

|  | Tablet strength (mg MTC/tablet) | | | | | |
|---|---|---|---|---|---|---|
|  | 50 mg | 50 mg | 50 mg | 75 mg | 75 mg | 75 mg |
| Ingredient | | | mg/tablet | | | |
| MTC (free base equivalent) | 73.6 | 73.6 | 73.6 | 110.41 | 110.41 | 110.41 |
| Microcrystalline cellulose (Avicel PH 102) | 115 | | | 172.5 | | |
| Spray-dried lactose | 26.9 | 141.9 | | 40.35 | 212.85 | |
| Spray-dried mannitol | | | 141.9 | | | 212.85 |
| Crosslinked polyvinylpyrrolidone | 7.5 | 7.5 | 7.5 | 11.25 | 11.25 | 11.25 |
| Magnesium Stearate | 2 | 2 | 2 | 3.00 | 3.00 | 3.00 |
| TOTAL TABLET WEIGHT/mg | 225 | 225 | 225 | 337.5 | 337.5 | 337.5 |

The MTC (Form A) and excipients were blended in a tumbling blender, and then compressed using a tablet machine.

Similar formulations may be prepared by a dry granulation method. The mix of excipients may alternatively be dry granulated using a roller compactor and then milled with an oscillating granulator using a 20 mesh screen. In that case, half of magnesium stearate may be used prior to roller compaction and half of the magnesium stearate is added to the granues and blended prior to compression on a conventional tablet machine. The tablet cores may then be film coated with an aqueous suspension of Opadry blue (registered trademark of Colorcon for a series of film coating systems).

EXAMPLE 6

Preparation of MTC Tablets by Direct Compression

Tablets having the following compositions were prepared by a direct compression method:

|  | Tablet strength (mg MTC/tablet) | | | |
|---|---|---|---|---|
|  | 25 | 50 | 75 | 100 |
| Ingredient | | mg/tablet | | |
| MTC (free base equivalent) | 36.80 | 73.60 | 110.43 | 147.24 |
| Microcrystalline cellulose (Avicel PH 102) | 230 | 230 | 230 | 230.00 |
| Spray-dried Lactose | 149.20 | 112.40 | 75.57 | 38.76 |
| Croscarmellose sodium | 30.00 | 30.00 | 30.00 | 30.00 |
| Magnesium stearate | 4.00 | 4.00 | 4.00 | 4.00 |
| TOTAL TABLET WEIGHT/mg | 450 | 450 | 450 | 450 |

Properties of the tablets were as follows:

| Tablet strength (mg) | Hardness range (kg) | Thickness range (mm) | Mean weight of 20 tablets (mg) | Table weight range of 20 tablets (mg) | Disintegration time (min) |
|---|---|---|---|---|---|
| 25 | 13.4-16.4 | 4.8-4.9 | 451 | 447-455 | 2 |
| 50 | 14.31-18.60 | 4.8 | 451.77 | 446-455 | 1.5 |

-continued

| Tablet strength (mg) | Hardness range (kg) | Thickness range (mm) | Mean weight of 20 tablets (mg) | Table weight range of 20 tablets (mg) | Disintegration time (min) |
|---|---|---|---|---|---|
| 75 | 19.5-22.0 | 4.7-4.9 | 451.5 | 445-458 | 1.5 |
| 100 | 19.2-23.8 | 4.8-5.1 | 451 | 446-457 | 1.5 |

EXAMPLE 7

Manufacture of MTC Trihydrate (Mixture of Tetra and Di-Hydrate) Tablets by Direct Compression and Dry Granulation a) MTC 30 mg tablets; prepared by direct compression with microcrystalline cellulose (155 mg/tablet), spray dried lactose (50 mg) and sodium starch glycolate; 250 mg round:

| Ingredient | Function | mg/tablet |
|---|---|---|
| MTC (expressed as trihydrate) | Drug | 30.0 |
| Microcrystalline cellulose (Avicel PH 102) | Diluent | 155.0 |
| Spray-dried lactose | Diluent | 50.0 |
| Sodium starch glycolate | Disintegrant | 12.5 |
| Magnesium stearate | Lubricant | 2.5 |

The blended material was compressed to a tablet weight of 250 mg at three different pressures. Properties of the resulting tablets were:

|  | Pressure 1 | Pressure 2 | Pressure 3 |
|---|---|---|---|
| Weight, mean | 249 mg | 250 mg | 251 mg |
| Hardness, mean | 10.8 kg | 14.5 kg | 15.3 kg |
| Thickness, mean | 4.5 mm | 4.3 mm | 4.3 mm |
| Disintegration time, mean | 50 seconds | 2.40 minutes | 1 minute |
| Friability | 2% | 0.39% | 1.3% | b) MTC 30 mg tablets; prepared by direct compression with microcrystalline cellulose and croscarmellose sodium; tablet weight 250 mg

| Ingredient | Function | mg/Tablet |
|---|---|---|
| MTC (expressed as trihydrate) | Drug | 30.0 |
| Microcrystalline cellulose (Avicel PH 102) | Diluent | 191.0 |
| Croscarmellose sodium | Disintegrant | 25.0 |
| Magnesium stearate | Lubricant | 2.5 |
| Colloidal silica (Aerosil 200) | Glidant | 1.5 |

The blended material was compressed to a tablet weight of 250 mg. Properties of the resulting tablets were:

| Parameter | Result |
|---|---|
| Description | Blue round tablet |
| Thickness range mm | 4.3-4.4 |
| Hardness range | 5.0-10.5 kg |
| Weight range for 20 tablets | 212-270 mg |
| Mean weight of 20 tablets | 247.51 mg |
| Friability | 0.26% |
| Disintegration time | 1 to 5 minutes | c) MTC 30 mg tablets; prepared by direct compression with microcrystalline cellulose, spray dried lactose and croscarmellose sodium; tablet weight 250 mg:

| Ingredient | Function | mg/tablet |
|---|---|---|
| MTC (expressed as trihydrate) | Drug | 30.0 |
| Microcrystalline cellulose (Avicel PH 102) | Diluent | 100.0 |
| Lactose spray dried | Diluent | 92.5 |
| Croscarmellose sodium | Disintegrant | 25.0 |
| Magnesium stearate | Lubricant | 2.5 |

The blended material was compressed to a tablet weight of 250 mg. Properties of the resulting tablets were:

| Parameter | Result |
|---|---|
| Description | Blue round tablets |
| Thickness, mean | 4.8 mm |
| Hardness, mean | 7.5 kg |
| Hardness range for 20 tablets | 6.0 to 8.8 kg |
| Weight of 20 tablets, mean | 248.4 mg |
| Friability | 0.31% |
| Disintegration time, mean | About 1 minute | d) MTC 30 mg tablets; prepared by direct compression method with microcrystalline cellulose and croscarmellose sodium; 210 mg round:

| Ingredient | Function | mg/tablet |
|---|---|---|
| MTC (expressed as trihydrate) | Drug | 30.000 |
| Microcrystalline cellulose (Avicel PH 102) | Diluent | 161.000 |
| Croscarmellose sodium | Disintegrant | 16.875 |
| Magnesium stearate | Lubricant | 2.125 |

The blended material was compressed to a tablet weight of 210 mg. Properties of the resulting tablets were:

| Parameter | Result |
|---|---|
| Weight | 202.5 mg |
| Hardness, mean | 7.9 kg |
| Thickness, mean | 4.2 mm |
| Disintegration time, mean | 36 seconds |
| Friability | 0.13% |

The disintegrant used can be replaced by crospovidone without affecting compressibility, disintegration and dissolution properties.

e) MTC 60 mg tablets; prepared by direct compression with microcrystalline cellulose, and croscarmellose sodium; 420 mg oblong:

| Ingredient | Function | mg/tablet |
|---|---|---|
| MTC (expressed as trihydrate) | Drug | 60.00 |
| Microcrystalline cellulose (Avicel PH 102) | Diluent | 322.00 |
| Croscarmellose sodium | Disintegrant | 33.75 |
| Magnesium stearate | Lubricant | 4.25 |

The blended material was compressed to a weight of 420 mg (Oblong tablets). Properties of the resulting tablets were:

| Parameter | Result |
| --- | --- |
| Weight, mean | 420.1 mg |
| Hardness mean | 12.9 Kg |
| Thickness mean | 5.2 mm |
| Disintegration time mean | 50 seconds |
| Friability | 0.1% |

EXAMPLE 8

Preparation of MTC Tablets by Dry Granulation (Slugging) Method a) MTC 30 mg tablets; prepared by slugging method with microcrystalline cellulose, lactose monohydrate 50 mg and sodium starch glycolate; tablet weight 250 mg:

| Ingredient | Function | mg/tablet |
| --- | --- | --- |
| MTC (expressed as trihydrate) | Drug | 30.0 |
| Microcrystalline cellulose (Avicel PH 102) | Diluent | 155.0 |
| Lactose monohyderate | Diluent | 50.0 |
| Sodium starch glycolate | Disintegrant | 12.5 |
| Magnesium stearate | Lubricant | 2.5 |

Method of Manufacture:
1. MTC and other ingredients were passed through a 30 mesh screen.
2. MTC, microcrystalline cellulose, lactose, half portion of sodium starch glycolate and half portion of magnesium stearate were blended.
3. The blended material was compressed into slugs on a tablet machine and the slugs were crushed through a 16 mesh screen.
4. The crushed material and remaining half portion of sodium starch glycolate and magnesium stearate were blended.
5. The blended material was compressed at a tablet weight of 250 mg.

The resulting tablets had the following properties:

| Parameter | Result |
| --- | --- |
| Description | Blue round tablets |
| Thickness range | 4.5-4.6 mm |
| Hardness range | 7.1-10.1 kg |
| Weight of 20 tablets, mean | 252.03 mg |
| Friability | 0.22% |
| Disintegration time | 2.0-2.5 minutes |

EXAMPLE 9

Preparation of MTC Tablets by Moist Granulation of Excipients and Incorporation of MTC Extra-Granularly a) MTC 30 mg tablets; prepared by granulating excipients and adding MTC extra-granularly with sodium starch glycolate:

| Ingredient | Function | mg/tablet |
| --- | --- | --- |
| MTC (expressed as trihydrate) | Drug | 30.0 |
| Microcrystalline cellulose (Avicel PH 102) | Diluent | 150.0 |
| Lactose monohydrate | Diluent | 42.5 |
| Povidone (K30) | Binding Agent | 12.5 |
| Sodium starch glycolate | Disintegrant | 12.5 |
| Magnesium stearate | Lubricant | 2.5 |

Method of Manufacture:
1. Lactose and microcrystalline cellulose (Avicel PH 102) were mixed.
2. Povidone (Plasdone K30) was dissolved in 200 ml deionised water.
3. Povidone (Plasdone) granulating solution of step 2 was added to lactose and microcrystalline cellulose mix from step 1.
4. The wet mass was passed through a 12 mesh screen.
5. The wet mass was dried.
6. The dried mass was passed through a 16 mesh screen to produce dried granules.
7. MTC, sodium starch glycolate and magnesium stearate were passed through a 30 mesh screen.
8. The above materials were blended with dried granules from step 7.
9. The blended material was compressed at a tablet weight of 250 mg.

The resulting tablets had the following properties:

| Parameters | Results |
| --- | --- |
| Description | Blue round tablets |
| Thickness | 4.5-4.6 mm |
| Hardness | 12.0-16.4 kg |
| Tablet weight range (20 tablets) | 245-254 mg |
| Friability loss | Less than 0.1% | b) MTC 30 and 60 mg tablets; prepared by granulating excipients and adding MTC extra-granularly) with croscarmellose sodium; 210 mg round

| | Tablet strength (mg MTC/tablet) | |
| --- | --- | --- |
| Ingredient | 30 mg | 60 mg |
| MTC (expressed as trihydrate) | 30 mg | 60 mg |
| Microcrystalline cellulose, Avicel PH 102 | 92.5 mg | 77.5 mg |
| Lactose monohydrate | 60 mg | 45 mg |
| Povidone (Plasdone K30) | 2.5 mg | 2.5 mg |
| Croscarmellose sodium | 22.5 | 22.5 mg |
| Magnesium stearate | 2.5 mg | 2.5 mg |

Prepared by a method similar to Example 9a).

EXAMPLE 10

Dissolution Studies

The rate and extent to which the active ingredient is absorbed from a pharmaceutical dosage form and becomes available at the site of action is defined as bioavailability (Chen, M. L. et al. Bioavailability and bioequivalence: an FDA regulatory overview, Pharm. Res. 2001, 18, 1645-1648). However, it is rarely feasible to measure the drug at the site of action. Therefore, bioavailability is assessed based on drug concentrations in the general circulation. The systemic exposure is determined by measuring the blood or plasma concentrations of the active drug at numerous time points following the drug administration and calculation of the area under the concentration-time curve (AUC). Blood/plasma drug concentration time profiles are affected by the dynamics of dissolution, solubility, absorption, metabolism, distribution, and elimination.

Absorption from a solid oral dosage form after administration can depend on the dissolution of the solid oral dosage form, which results from a series of simultaneous and successive processes, and the permeability across the gut wall of the gastrointestinal tract. Depending on the classification of the drug substance under the Biopharmaceutical Classification System (high solubility/high permeability; high solubility/low permeability; low solubility/high permeability; low solubility/low permeability), in vitro dissolution may be relevant to the prediction of in vivo plasma concentrations and therefore bioavailability (Guidance for Industry, Dissolution Testing of Immediate Release Solid Oral Dosage Forms, U.S. Department of Health and Human Services, Food and Drug Administration, Center for Drug Evaluation and Research (CDER), August 1997).

Based on this general consideration, in vitro dissolution tests for immediate release solid oral dosage forms, such as tablets and capsules, are used to assess the quality of a drug product. An immediate release product allows the ingredient or active moiety to dissolve in the gastrointestinal tract, without causing any delay or prolongation of the dissolution or absorption of the drug. Requirements for dissolution testing of immediate release products are set out in the Guidance for Industry (CDER 1997) "Dissolution testing for immediate release solid oral dosage forms", (CDER 1997) "Immediate release solid oral dosage forms—Scale up and Postapproval Changes", ICH Guidance Q6A, Specifications: Test Procedures and Acceptance Criteria For New Drug Substances And New Drug Products. The most commonly employed dissolution test methods as described in the USP and European Pharmacopeia (6th edition) are the basket method (USP 1) and the paddle method (USP 2). The described methods are simple, robust, well standardized, and used worldwide. They are flexible enough to allow dissolution testing for a variety of drug products. The following parameters influencing the dissolution behaviour may for example be relevant for selecting the appropriate in vitro dissolution test conditions for an immediate release solid oral product: apparatus, stirring speed, dissolution medium and temperature. Because of the biopharmaceutical properties of MTC and its expected desirable absorption characteristics in the upper gastrointestinal tract, it was preferable to produce rapidly dissolving tablets of MTC.

Compositions according to the invention can be dissolution tested in a USP-2 apparatus in 900 ml of 0.1 N HCl, with paddles rotating at 50-75 rpm. Compositions according to the invention exhibit at least the acceptance criteria cited for Stage 1 (S1) testing in the USP 32 (The United States Pharmacopeia, edited by the United States Pharmacopeial Convention, Inc., 12601 Twinbrook Parkway, Rockville, Md. 20852; Published by Rand McNally, Inc., 32nd Edition, 2008):

Acceptance Criteria: Each tablet achieved 85% dissolution of MTC within 30 minutes after insertion of the coated tablet into the 0.1 N HCl.

EXAMPLE 11

Film Coating of MTC Tablets a) Aqueous Film Coating—Method 1

The coating pan was warmed without the tablets for 10-15 minutes with an inlet air temperature between 45° C. and 75° C., preferably 50-65° C., until the exhaust temperature reaches 35-55° C., preferably 40-50° C. The MTC tablets were sprayed with the aqueous film coat at a spray rate such that the bed temperature is maintained at 38-48° C., preferably 42-44° C. Once the required weight gain was achieved, spraying was stopped and the temperature inlet control was switched off. The tablets were allowed to cool on a jog cycle until bed temperature reached room temperature.

A similar method may be used for non-aqueous film coating.

b) Aqueous Film Coating—Method 2

The coating pan was warmed with the tablets for 10 minutes with an inlet air temperature around 50° C., preferably around 40° C., until the bed temperature reached 30-45° C., preferably 35-40° C. The MTC tablets were sprayed with the aqueous film coat at a starting spray rate such that the bed temperature was maintained at 28-44° C., preferably 30-35° C. Once around 1% weight gain had been achieved, the inlet temperature was increased to around 50° C., preferably 45° C., the spray rate was used to keep the bed temperature at 28-44° C., preferably 35-40° C. Once around 2% weight gain was achieved, the inlet temperature was increased to around 60° C., preferably 50° C., and the spray rate increased to keep the bed temperature at 28-44° C., preferably 35-40° C. Once the required weight gain was achieved, spraying was stopped and the temperature inlet control was switched off. The tablets were allowed to cool on a jog cycle until the bed temperature reached room temperature.

A similar method may be used for non-aqueous film coating.

An example of a tablet formulation that may be film-coated by one of the above methods is:

| Ingredient | mg/tablet |
| --- | --- |
| MTC | 147.24 |
| MCC | 230.00 |
| Spray-dried lactose | 38.76 |
| Crosscarmelose sodium | 30.00 |
| Magnesium stearate | 4.00 |
| Tablet weight | 450.00 |

EXAMPLE 12

Analysis of MTC Polymorphic Forms by XRPD after Long-Term Storage of Tablets

MTC tablets were manufactured at various tablet strengths, stored under controlled conditions of temperature and relative humidity, and the polymorphic forms analysed by XRPD:

MTC Form A tablets; stored in aluminium blisters

| Tablet strength | Storage conditions | Storage time/ months | Polymorphic form |
| --- | --- | --- | --- |
| 50 mg | 25° C./ 65% RH | 10.5 | A |
| 25 mg | 25° C./ 65% RH | 9 | A |
| 25 mg | 40° C./ 75% RH | 6 | A |

EXAMPLE 13

Preparation of MTC Capsules

MTC capsules, for example in Gelatin or HPMC, may be prepared using compositions of MTC with diluents, disintegrants and lubricants which may be qualitatively similar to those discussed above in respect of the tablet formulations. An example capsule composition containing 25, 50, 75, 100 mg of MTC as free base equivalent in Gelatin or HPMC capsule shells is as follows:

| Ingredient | Function | Capsule strength in (mg of MTC) | | | |
| --- | --- | --- | --- | --- | --- |
| | | 25 | 50 | 75 | 100 |
| | | mg/capsule | | | |
| MTC (free base equivalent) | Drug | 36.80 | 73.61 | 110.41 | 147.22 |
| Spray-dried mannitol | Diluent | 238.70 | 201.89 | 165.09 | 128.28 |
| Cross-linked polyvinyl-pyrrolidone | Disintegrant | 3.00 | 3.00 | 3.00 | 3.00 |
| Magnesium stearate | Lubricant | 1.50 | 1.50 | 1.50 | 1.50 |
| Total | | 280.00 | 280.00 | 280.00 | 280.00 |

It will be appreciated that alternative diluents, disintegrants and lubricants can be used in place of those described above, which may be (by way of non-limiting example) any of those described in the Examples above—e.g. Example 5 (Avicel, spray-dried lactose), Example 6 (Croscarmellose sodium), Example 7 (sodium starch glycolate) and so on.

The invention claimed is:

1. A tablet pharmaceutical composition in solid dosage form comprising:
   (a) substantially pure and stable polymorph Form A methylthioninium chloride ("MTC"),
   (b) at least one diluent suitable for direct compression selected from microcrystalline cellulose or a sugar,
   (c) optionally further comprising a coating and
   (d) optionally one or more other excipients,
   wherein the amount of MTC in the composition is 10-75% w/w of the weight of composition without the coating, and
   wherein the composition is obtained by a process comprising dry compression of an intimate powder mixture of the MTC in a substantially pure polymorphic form with the at least one diluent suitable for direct compression.

2. A composition as claimed in claim 1, wherein the amount of MTC in the composition is 10-50% w/w of the weight of the composition without the coating.

3. A composition as claimed in claim 2, wherein the amount of MTC is 10-40% w/w of the weight of the composition without the coating.

4. A composition as claimed in claim 3, wherein the amount of MTC in the composition is from 10-35% w/w of the weight of the composition without the coating.

5. A composition as claimed in claim 1, which comprises at least 15% w/w of diluent(s) of the weight of the composition without the coating.

6. A composition as claimed in claim 5, wherein the diluent(s) are selected from the group consisting of microcrystalline cellulose, lactose, and mannitol.

7. A composition as claimed in claim 1, which further comprises a lubricant.

8. A composition as claimed in claim 7, wherein the lubricant is selected from the group consisting of magnesium stearate, calcium stearate, and stearic acid.

9. A composition as claimed in claim 7, wherein the lubricant is magnesium stearate.

10. A composition as claimed in claim 7, which comprises from about 0.5 to about 2.0% w/w lubricant based on the weight of the composition without the coating.

11. A composition as claimed in claim 1, which further comprises one or more disintegrants selected from the group consisting of crosslinked polyvinylpyrrolidone, sodium starch glycolate, crosslinked sodium carboxymethyl cellulose (sodium croscarmellose), and pregelatinized starch.

12. A composition as claimed in claim 1, which further comprises a binder selected from the group consisting of (carboxymethylcellulose, hydroxypropyl methylcellulose, hydroxypropyl cellulose, hydroxyethylcellulose, ethylcellulose, microcrystalline cellulose, lactose, sucrose, dextrose, glucose, maltodextrin, mannitol, xylitol, polymethacrylate, polyvinylpyrrolidone, sorbitol, pregelatinized starch, alginic acids, sodium alginate, magnesium aluminum silicate, and polyethylene glycol.

13. A composition as claimed in claim 1, further comprising a film coating.

14. A composition as claimed in claim 13, wherein the film coating comprises hydroxypropylmethylcellulose (HPMC) or polyvinyl alcohol-part hydrolysed (PVA).

15. A method of treatment of a tauopathy in a patient, said method comprising administering to said patient a therapeutically-effective amount of a solid dosage form composition of claim 1.

16. A composition according to claim 1, wherein the dry compression comprises direct compression using a tablet machine.

17. A composition according to claim 1, wherein in said process, prior to the dry compression of the intimate powder mixture, the MTC and the least one diluent suitable for direct compression are formed into a compressed mass, wherein the compressed mass is milled to form dry granules, which are then compressed using a tablet machine.

18. A composition according to claim 1, wherein in said process, prior to formulation of the intimate mixture, the diluent(s) are (i) mixed in the presence of a granulating fluid to form a wet mass, and (ii) the wet mass is then dried to form granules of the diluent(s), wherein said granules of the diluent(s) are subsequently blended with the MTC and compressed to form a tablet.

19. A process for the manufacture of a pharmaceutical composition according to claim 1,
    which process comprises
    (a) mixing
       (i) substantially pure and stable polymorph Form A methylthioninium chloride ("MTC"), with
       (ii) at least one diluent suitable for direct compression selected from microcrystalline cellulose or a sugar, and, optionally
       (iii) one or more further excipients to form an intimate powder mixture; and
    (b) dry compression of the intimate powder mixture.

20. A process as claimed in claim 19, wherein the dry compression comprises direct compression using a tablet machine.

21. A process as claimed in claim 19, wherein prior to the dry compression of the intimate powder mixture, the MTC and the at least one diluent suitable for direct compression are formed into a compressed mass, wherein the compressed mass is milled to form dry granules, which are then compressed using a tablet machine.

22. A process as claimed in claim 19, wherein, prior to formation of the intimate mixture, the diluent(s) are (i) mixed in the presence of a granulating fluid to form a wet mass, and (ii) the wet mass is then dried to form granules, wherein said granules of the diluent(s) which are subsequently blended with MTC and compressed to form tablets.

23. A process as claimed in claim 19, which further comprises the step of applying a film coating to the tablets.

24. A process as claimed in claim 23, wherein the step of applying a film coating is carried out in a coating pan and comprises pre-heating of the coating pan, prior to introduction of the tablets to be coated.

25. A process as claimed in claim 24, wherein the temperature of the tablets is maintained during coating at a temperature of 38-48° C.

26. A process as claimed in claim 24, wherein the temperature of the tablets is maintained during coating at a temperature of 42-44° C.

* * * * *